(12) United States Patent
Hansen

(10) Patent No.: US 8,674,166 B2
(45) Date of Patent: Mar. 18, 2014

(54) THIN FILM DRESSING

(75) Inventor: Grazyna Hansen, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 418 days.

(21) Appl. No.: 12/514,584

(22) PCT Filed: Nov. 12, 2007

(86) PCT No.: PCT/DK2007/000491
§ 371 (c)(1),
(2), (4) Date: May 13, 2009

(87) PCT Pub. No.: WO2008/058535
PCT Pub. Date: May 22, 2008

(65) Prior Publication Data
US 2010/0063435 A1    Mar. 11, 2010

(30) Foreign Application Priority Data

Nov. 13, 2006  (DK) ................................ 2006 01478
Jun. 15, 2007  (DK) ................................ 2007 00867

(51) Int. Cl.
*A61F 15/00*    (2006.01)
(52) U.S. Cl.
USPC .................. 602/54; 602/41; 602/42; 602/43; 602/52; 602/58
(58) Field of Classification Search
USPC .............................. 602/54, 41–43, 52, 57–58
See application file for complete search history.

(56) References Cited

U.S. PATENT DOCUMENTS

| 4,367,732 A | | 1/1983 | Poulsen et al. | |
| 4,867,748 A | | 9/1989 | Samuelsen | |
| 5,051,259 A | | 9/1991 | Olsen et al. | |
| 6,159,497 A | * | 12/2000 | LaPrade et al. | ............... 424/448 |
| 2007/0065574 A1 | * | 3/2007 | Rosati et al. | ............... 427/207.1 |

FOREIGN PATENT DOCUMENTS

| DK | 127578 | 12/1973 |
| DK | 148408 | 12/1982 |
| DK | 147226 | 5/1984 |
| DK | 154806 | 6/1988 |
| DK | 154747 | 12/1988 |
| DK | 169711 | 1/1995 |

(Continued)

OTHER PUBLICATIONS

E. Gomez-Panzani et al., "Application and maintenance habits to make a difference in adhesion of Alora transdermal systems", Maturitas 35 (2000) 57-64, (p. 61, table 2).*

*Primary Examiner* — Patricia Bianco
*Assistant Examiner* — Caitlin Carreiro
(74) *Attorney, Agent, or Firm* — Jacobson Holman PLLC

(57) ABSTRACT

The invention relates to a thin film dressing having a release liner which is able to support the dressing during application. The resilience or stiffness of the release liner is higher than the resilience or stiffness of the dressing so as to enable the control of the dressing during application. The invention further relates to a method of application of the thin film dressing where a minor part of the dressing initially is applied to the skin afterwards the dressing is folded backwards so the release liner faces upwards. Finally, the remaining part of the dressing is applied by pushing the release liner forwards in a rolling motion thereby rolling the dressing onto the skin. This dressing assembly allows the dressing to be applied by using only one hand.

19 Claims, 3 Drawing Sheets

(56) References Cited

FOREIGN PATENT DOCUMENTS

| EP | 0097846 | 1/1984 | |
| EP | 0409587 | 1/1991 | |
| EP | 0415183 | 3/1991 | |
| EP | 0434258 | 6/1991 | |
| EP | 434258 A2 * | 6/1991 | ............. A61F 13/02 |
| EP | 0465023 | 1/1992 | |
| EP | 465023 A1 * | 1/1992 | ............. A61F 13/02 |
| GB | 1280631 | 6/1972 | |
| NO | 157686 | 1/1988 | |
| SE | 365410 | 3/1974 | |
| WO | WO 88/06894 | 9/1988 | |
| WO | WO/91/01706 | 2/1991 | |
| WO | WO 9101706 A1 * | 2/1991 | ............. A61F 13/02 |
| WO | WO 2004/060225 | 7/2004 | |

\* cited by examiner

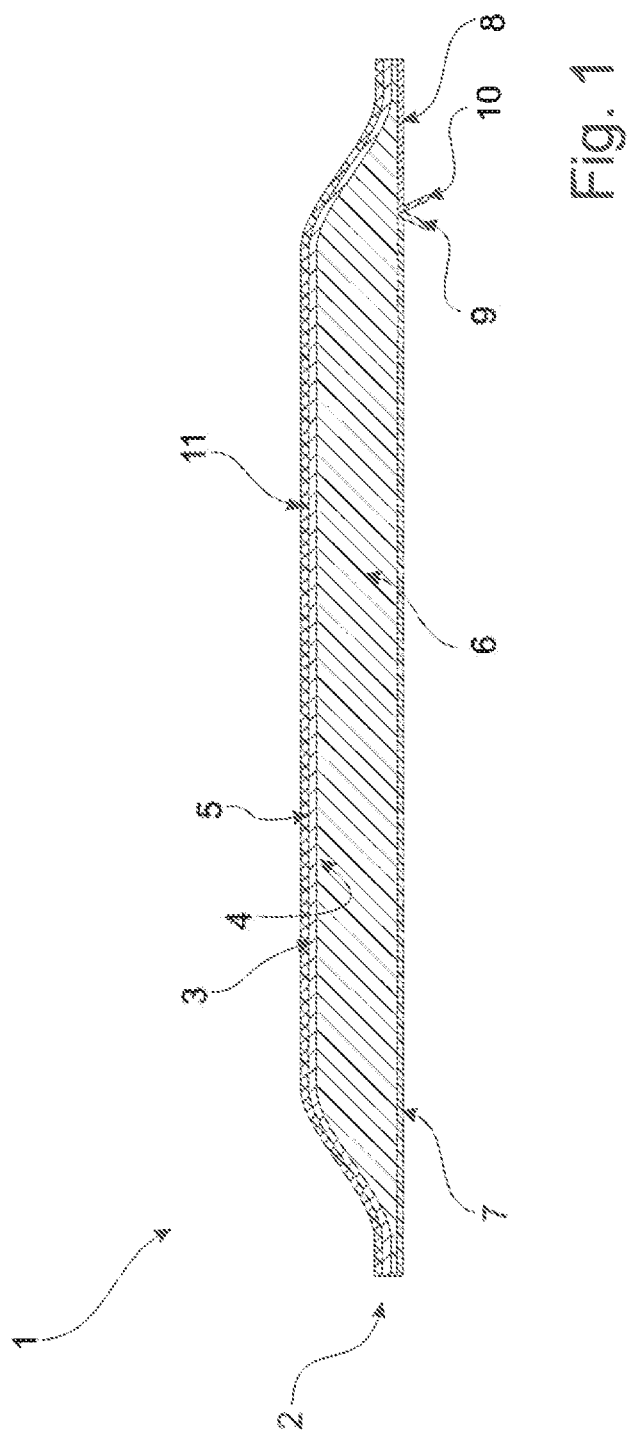

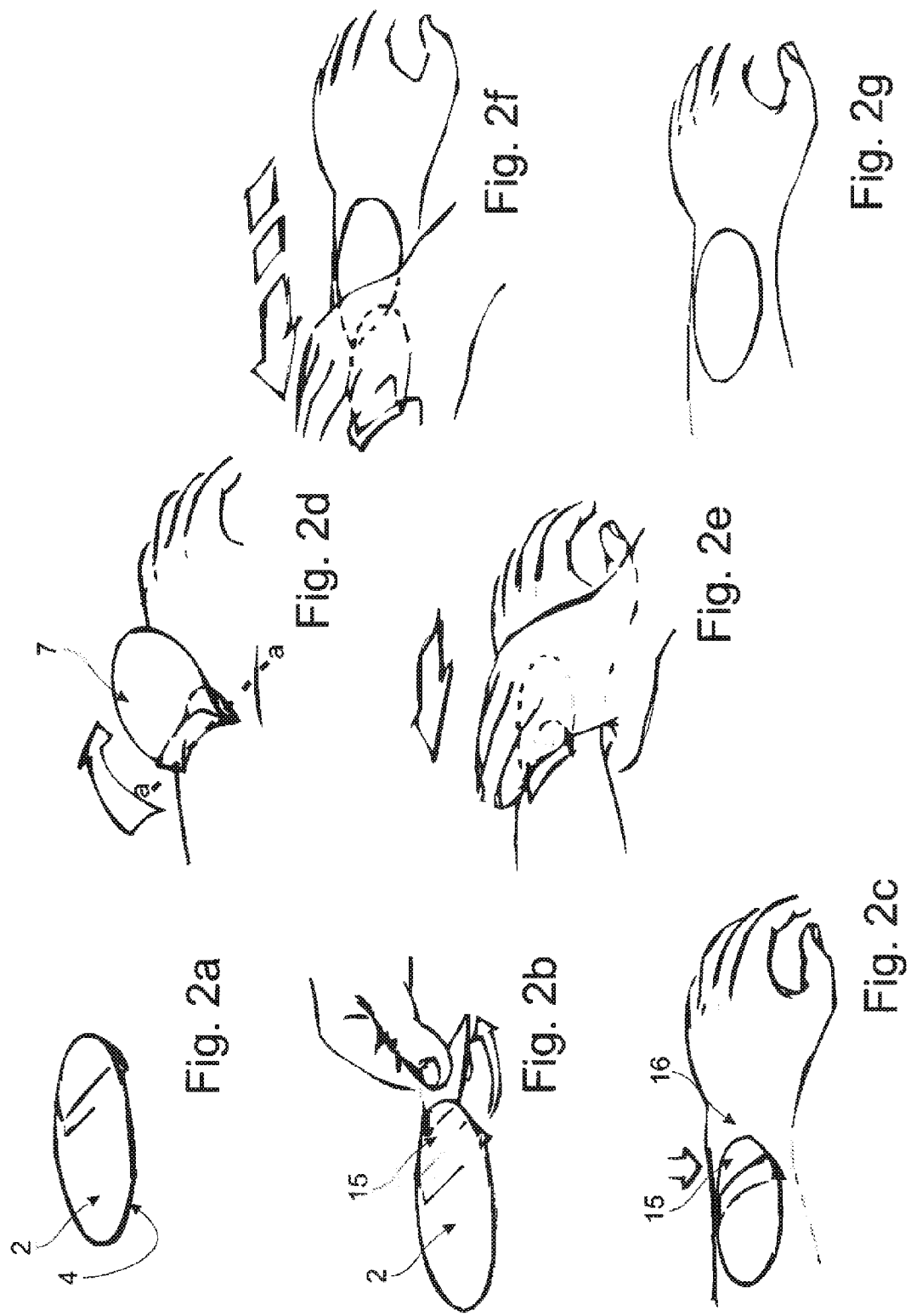

THIN FILM DRESSING

The invention relates to thin film dressings and more particular to a thin film dressing having a release liner that is able to support the dressing during application.

BACKGROUND

Thin film dressings are particularly advantageous as an extra skin, where the normal skin needs protection for a shorter or longer period, e.g. as a result of affection by psoriasis, burns or other wounds. Typically, the thin dressings will be capable of following the surrounding skin as it stretches or folds and hence would not be uncomfortable to wear. However, this effect, which is beneficiary when the dressing is in place on the skin, makes it difficult to apply the dressing. This is due to the tendency of the dressing to roll and wrinkle or maybe even attach to itself during application caused by the flimsiness of the dressing.

EP0434258 provides a thin film dressing assembly which has two equally sized release liners. Each of the release liners is longer than the dressing and are folded in half with the lower half adhering to the dressing and the upper half projecting a short distance beyond the edge of the dressing leaving free ends of the release liners at the edges. The release liners are less flexible than the dressing so as to maintain the dressing in flat condition and wrinkle-free during application. Application of the dressing is done by holding the dressing assembly up to the skin with the exposed parts of the release liners touching the skin and then pulling at the free ends of the release liners outwardly and parallel to the dressing and the skin.

However, there is still a need for a thin film dressing which is controllable during application.

SUMMARY OF THE INVENTION

The invention relates to a dressing assembly comprising a thin film dressing with an adhesive disposed on a backing layer and where the assembly further comprises a stiffening release liner which supports the thin film in application of the dressing. The backing of the thin film dressing has a thickness of less than 300 µm. The stiffness or rigidity of the entire dressing assembly (including the release liner) derives mainly from the release liner, as the dressing itself contributes very little to the stiffness.

The release liner with a higher rigidity than the dressing will be able to support the dressing during application and hence prevent wrinkling or adhering of the dressing to itself. As the supportive release liner covers the major part of the dressing, it is possible to apply the dressing using only one hand. This is due to the fact that the major part of the dressing not already applied to the skin will be covered by the supporting release liner at all times during application.

The invention also relates to a method of applying a thin film dressing in which a smaller part of the dressing initially is adhered to the skin while the major part of the release liner still is present on the dressing. Following the initial attachment of the smaller part of the dressing, the dressing assembly is folded backwards and the release liner is pushed off in the direction of application, while rolling the dressing onto the skin.

The peel value between the release liner and the thin film dressing has a value so that it is possible with relative ease to push the release liner off the dressing.

DETAILED DISCLOSURE OF THE INVENTION

One aspect of the invention relates to an adhesive dressing assembly comprising a dressing comprised of an adhesive disposed on a backing layer, and the dressing assembly further comprises at least one supportive release liner covering the major part of the adhesive surface of the dressing, wherein
  the dressing has a thickness less than 300 µm,
  the rigidity of the supportive release liner is higher than the rigidity of the dressing and
  the peel-value is such that the release liner is able to be easily pushed off the adhesive.

By a supportive release liner is meant a release liner, which has a stiffness or rigidity enabling it to support the dressing during application. That is the stiffness or rigidity of the supportive release liner is higher than the corresponding values of the dressing.

The balance between the peel-value making it relatively easy to push off the supportive release liner and the rigidity of the release liner provides a dressing, which will be easy to control during application, as the supportive release liner will provide the necessary support and stiffness to the thin film during attachment of the dressing to the skin. Then the dressing will have a reduced tendency to wrinkle or to enclose air bubbles between the dressing and the skin during application. The wrinkles or enclosed air bubbles are further reduced to the peel value of the dressing assembly being low, which will prevent the dressing from stretching during application. Wrinkles or enclosed air bubbles are undesirable, as the dressing will have folds caused by the bubbles or wrinkles. If the dressing is touched or subjected to a light pressure, e.g. from folds in clothing, the folds of the dressing may enhance pressure on the damaged skin consequently causing further damage to the skin.

The adhesive may be any skin-friendly adhesive known per se, e.g. an adhesive comprising hydrocolloids or other moisture absorbing constituents for prolonging the time of use. The adhesive may suitably be of the type disclosed in GB patent specification No. 1 280 631, in DK patent specifications Nos. 127,578, 148,408, 154,806, 147,226 and 154,747, in EP published application Nos. 0 097 846 and 0 415 183, in SE published application No. 365,410, in WO publication No. 88/06894, in U.S. Pat. No. 4,867,748 and in NO published application No. 157,686. Especially preferred are the adhesives disclosed in U.S. Pat. Nos. 4,367,732 and 5,051,259 and DK patent specification No. 169,711.

In a preferred embodiment of the invention, the adhesive comprises a hydrocolloid adhesive. The use of a hydrocolloid adhesive may provide an excellent protection of the surrounding skin of the wound by inducing the moist wound healing environment and yet avoiding maceration. The thickness of the adhesive is preferably between 60 and 300 µm, more preferred between 60 and 200 µm. In an embodiment the adhesive layer is between 60 and 70 µm and in another embodiment the adhesive layer is between 110 and 130 µm.

The skin facing layer may also comprise any other adhesives, preferably pressure sensitive adhesives and/or hotmelts, chosen from a wide range of different types of adhesives for instance the acrylic types and types derived from PIB (Poly Isobutylene), polyurethanes, EVA-compounds (Ethyl-vinyl-acetate compounds), APAO's (Amorphous poly-alpha olephines), silicones, polyvinyl ether.

The release liner is used to protect the adhesive of the dressing and give the dressing the support it needs due to the flimsy nature of the dressing. It should also be easily peelable from the adhesive. The value should be such that the release liner can easily be pushed off the adhesive during application. On the other hand, the release liner should not be able to detach from the adhesive by itself.

The peel value determines how easily the release liner is rolled off the film sheet dressing. It is required that the peel value between the first supportive release liner and the adhesive of the dressing is relatively low, so that the dressing is easily applicable.

In one embodiment, where the dressing is highly stretchable and deformable, for example where the backing layer is formed of a polyurethane film whereon an adhesive is disposed, the peel value between the release liner and the dressing is set so that the dressing may be released without being stretched or otherwise deformed.

The peel value is preferably below 3 N/mm as measured as explained in the example relating to testing of peel value. The value should be above 0.02 N/mm so as to prevent the release liner from detaching by itself. Even more preferred the value is below 1.6 N/mm and most preferred approx. 0.1 N/mm.

In an embodiment the first supportive release liner covers the entire adhesive surface of the dressing, i.e. has coverage of 100%.

In other embodiments, it may be preferred that a part of the dressing is adhered prior to removing the first supportive release liner in order to provide an initial tack when the dressing is to be adhered to the skin. In these embodiments, it should be understood that the first supportive release liner covers a major part of the adhesive of the dressing, for example between 60% and 100%. Depending on the adhesive and the flexibility of the dressing the major part can cover the adhesive of the dressing anywhere between 60%, 65%, 70%, 75%, 80%, 85%, 90% or 95%; and 100%.

In one embodiment of the invention, the first supportive release liner has a stiffness, rigidity or resistance to stretching and bending which is greater than the respective stiffness, rigidity or resistance to stretching and bending the dressing. Such values, may for example be determined by the modulus of elasticity (MOE) for the release liner and the dressing.

The rigidity of the release liner should be of such a value that it would have fewer tendencies to bend or stretch particularly during application of the dressing. Thereby, it would ensure the supportive effect of the release liner.

The MOE may be measured in different ways. One way of measuring it is to apply the sample to be tested to tension and measuring the relationship between the load application and the elongation of the sample. From these data the MOE may be calculated. The MOE of the release liner is preferably between 200 N/mm and 600 N/mm when the modulus is measured as shown in the example relating to testing of modulus. The most preferred value is between 350 N/mm and 450 N/mm and most preferred approx. 400 N/mm.

The dressing assembly may be provided with more than one release liner, preferably two. In such an embodiment, the supportive release liner still covers the major part of the adhesive and the smaller release liner covers a smaller part. In a related embodiment, there may be two or more supportive release liners defining folding lines between them.

The release liners may be provided with one or more pulling tabs, so-called non-touch due to their purpose of being able to remove the release liners with minimal risk of touching the adhesive of the dressing. This simplifies gripping the release liner when the release liners are about to be removed.

The thickness of the release liner is preferably at least 40 µm, more preferred at least 60 µm, or at least 80 µm, even at least 100 µm or maybe up to 150 µm. The preferred values are between 45-95 µm, more preferred between 70 and 80 µm and the most preferred value is approx. 75 µm. This will provide the release liner with the necessary supportive effect. The release liner may be made of PE or alternatively PET.

The backing layer is the part of the dressing which during production functions as a support layer for the adhesive and acts as protection for the skin, when the dressing is in use according to its purpose. It is preferred that the backing layer has a thickness of at least 5-50 µm, preferably at least 10 µm or at least 20 µm or maybe 50 µm. The most preferred values are between 10 and 20 µm or between 25 and 35 µm. This provides the dressing with the necessary flexibility so that it follows the skin as the skin stretches and folds. The preferred materials of the backing layer are PU, PE or PET.

Dressings (backing layer with an adhesive disposed on it) having an adhesive layer of approx. 65 µm in combination with an extremely thin backing layer of e.g. approx. 15 µm, that is a dressing of a thickness of approx. 80 µm (such as between 75 and 85 µm), would provide a dressing, which is particularly useful for some purposes—e.g. sores as cold sores. Dressings having an adhesive layer of approx. 120 µm and a backing of approx. 30 µm (a dressing of a thickness of approx. 150 µm—such as between 140 and 160 µm) would provide for a very useful dressing for covering large areas, where the need for flexibility is extremely important.

The side of the backing layer, which in use faces the skin is the side covered with the adhesive, and is defined as the proximal or skin-facing side. The side facing away from the skin in use is defined as the distal side.

The MVTR value is between 0-250 mg/cm$^2$/day, preferably between 15 and 100 mg/cm$^2$/day and most preferred to 60 mg/cm$^2$/day. MVTR is the moisture vapour transition rate and by having a value of 60 mg/cm$^2$/day the dressing will be able to transport the moisture of the skin defect or wound through the dressing.

In a further embodiment, the dressing assembly comprises a top film covering the distal side of the backing layer. The purpose of the top film is to control the backing layer during manufacturing that is to control the backing layer as the adhesive is applied to the layer. However, during storage the top film also functions as a protection layer. The top film is preferably removed from the backing layer prior to application of the dressing. The top film is preferably made of paper and as it is only used temporarily during storage, the thickness of the top film is of less importance.

Another aspect of the invention relates to a method for application of a dressing to the surface of the skin, where the dressing comprises an adhesive disposed on the proximal side of a backing layer and a release liner covering at least a part of the adhesive of the dressing. The method comprises the following steps:

adhering a first part of the dressing to the surface of the skin, folding a second part of the dressing backwards around a folding line, so that the distal side of the backing layer faces the surface of the skin and the release liner faces away from the surface of the skin, and displacing the release liner in a direction transverse to the folding line, so that the second part of the dressing is released from the release liner.

The method of application of a dressing makes it possible to apply the dressing while using only one hand. This enables a patient to apply the dressing himself and particularly to apply the dressing to one of his arms.

In the following, it should be understood that reference to the proximal side of the dressing assembly, the dressing or any of the components thereof is a reference to the side, which faces or would face the skin of a user when the dressing is being applied. Thus, the distal side of the same element would be the side facing away from the skin when the dressing is being applied.

If the dressing comprises more than one release liner the smaller part, which may be non-supportive, is entirely removed. Otherwise, part of the supportive release liner is removed so as to expose a small part of the adhesive, which is then attached to skin. Where the release liner has a pulling tab this may be used to easily initiate the peeling off of the release liner. Alternatively, the peeling off may be initiated by using a fingernail.

When the smaller part of the dressing—corresponding to the first part of the dressing—is applied to the skin, the major part (or the second part) is folded backwards so the distal side of the dressing faces the skin. The dividing line between the adhesive and the release liner will then face the skin. The dressing may then be applied by pushing the release liner off the adhesive in a sliding, rolling motion using one hand only to apply a light pressure on the dressing towards the skin while at the same time pushing the release liner parallel to the skin. This may also be seen as a stroking motion. This way the pressure from the applying hand removes and prevents any wrinkles or bubbles from being trapped during application of the dressing.

This enables users even with poor dexterity to easily apply the dressing while using only one hand.

If the dressing assembly is provided with two or more supportive release liners, the dressing is again folded backwards at the dividing line between the supportive release liners. Afterwards, the second supportive release liner is removed following the same steps as used during removal of the first supportive release liner. This procedure is then followed until the dressing is completely adhered to the skin.

BRIEF DESCRIPTION OF THE DRAWINGS

In the following the invention is disclosed by more detailed examples with reference to the drawings, in which:

FIG. 1 shows in section, a dressing according to the invention,

FIG. 2 shows by illustration a method according to the invention whereby the dressing in FIG. 1 is applied.

DETAILED DESCRIPTION OF THE PREFERRED EMBODIMENTS

Figure 3A:
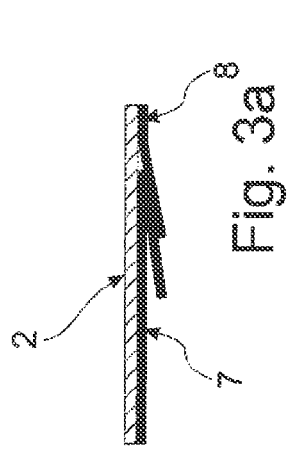
FIG. 3 shows in section the same as in FIG. 2.

The invention will in the following be explained more in detail with reference to the drawings showing the preferred embodiments of the invention.

In FIG. 1 the dressing assembly 1 is shown. The dressing assembly comprises a dressing 2, a first and a second release liner 7,8 and a top-film 11. The dressing 2 comprises a backing layer 3 having a proximal 4 and a distal side 5. On the proximal side 4 an adhesive layer 6 is disposed and the top-film 11 is arranged on the distal side 5.

The supportive first release liner 7 covers at least the major part of the adhesive layer 6, while the second release liner 8 covers the remaining smaller part of the adhesive layer 6.

In an alternative embodiment, the supportive release liner covers the entire surface of the adhesive layer.

Pulling tabs 9, 10 are provided on the release liners 7, 8. The pulling tabs 9, 10 allows for easy handling of the release liners 7, 8 with minimal risk of touching the adhesive layer 6 with the fingers.

FIGS. 2a-2g and FIGS. 3a-3g illustrate one embodiment of a method of applying the dressing 2 to the skin of a user. FIGS. 2a-2g illustrate this application in perspective using one hand. FIGS. 3a-3g illustrate the same application method seen in cross-section of the dressing.

FIGS. 2a and 3a show a dressing assembly as described in FIG. 1 where the top-film 11 has been removed. Furthermore, the backing layer and the adhesive are shown as one dressing unit 2 for simplicity of the drawing. On the proximal side of the dressing, a supportive first release liner 7 and a second release liner 8 are arranged. The first release liner 7 covers the major part of the proximal surface 4 of the dressing.

Figure 3B:
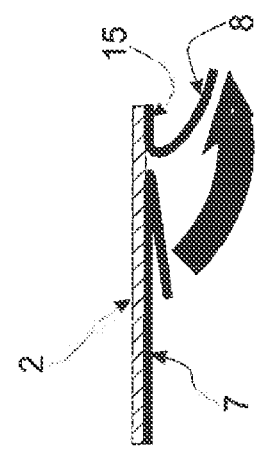

In FIGS. 2b and 3b the second release liner 8 is removed, exposing a small adhesive area 15 of the dressing 2.

Figure 3C:
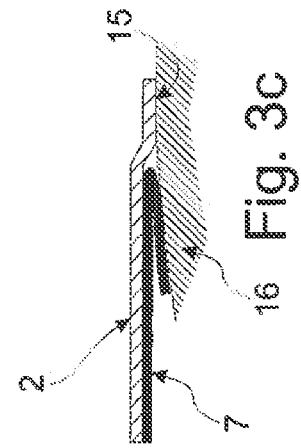

As shown in FIGS. 2c and 3c the small adhesive area 15 of the dressing is applied to the skin 16 of the user.

Figure 3D:
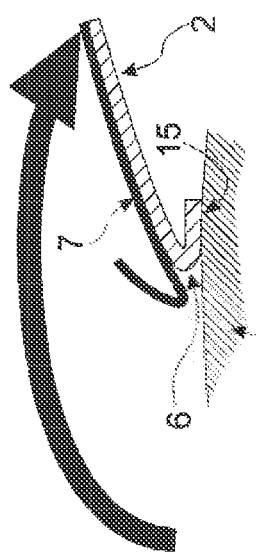
Figure 3E:
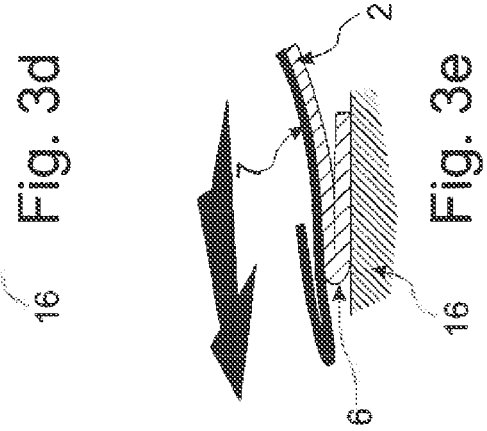
Figure 3F:
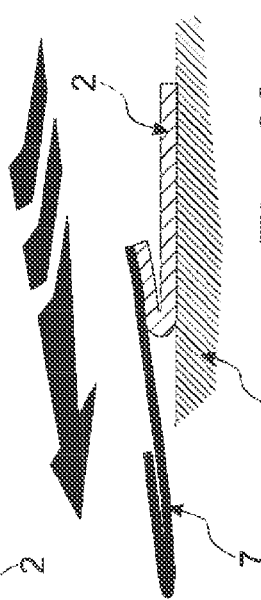

After applying the small adhesive area 15 to the skin the dressing is turned over backwards, i.e. it is folded around a folding line a-a as seen in FIGS. 2d and 3d so that the distal side 5 of the dressing which is not adhered to the skin faces the skin of the user.

As shown in FIGS. 2e, 2f, 3e and 3f the first supporting release liner 7 is subsequently displaced transverse to the folding line a-a separating the release liner 7 from the adhesive 6. While displacing in a direction mainly parallel to the skin, this step will at the same time continuously expose adhesive which subsequently is adhered to the skin, thereby applying the dressing in a continuous motion.

Figure 3G:
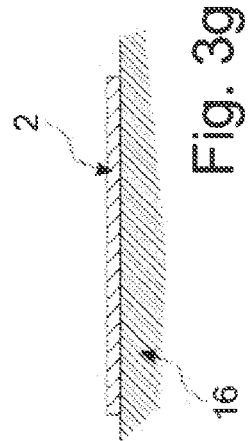

Thus, when the supporting first release liner 7 has been fully displaced, i.e. removed from the dressing, the dressing 2 has been evenly and easily applied to the skin of the user as shown in FIGS. 2g and 3g.

It should be understood that the above description is an exemplary embodiment and that many modifications and alternative embodiments may be provided within the scope of the invention.

Thus, the dressing assembly may for example be provided with only one release liner and a minor part of this is then initially removed.

Yet, alternatively the dressing assembly is put on the skin with the release liners touching the skin. The smaller second release liner is then entirely removed. Subsequently, the exposed part of the adhesive is applied to the skin; afterwards the dressing is folded backwards so that the distal side of the backing layer faces the skin. The major part of the dressing is now applied in a sliding, rolling motion transversely to the folding line while pushing the supportive release liner off the dressing as described above.

Example

Testing of Modulus of Elasticity

The MOE was tested on two samples. Sample 1 consisted of the release liner with a coating of silicone, 75 µm PETP (Polyethylene terephthalate) with 1720 silicone. Sample 2 consisted of the dressing (backing and adhesive) and the release liner with a coating of silicone: Backing PU-film 30 µm, rec. 96 (an adhesive) 120 µm, 75 µm PETP with 1720 silicone. The test was performed according to ISO 527-3 (1995): "Plastics—Determination of properties—part 3: Test Conditions for film and sheets."

The samples were tested in an Instron tensile machine, model 5569, load 5 and using a 0.1 kN load cell. The test speed was set at 1 mm/min. For measuring the MOE in tension (the tensile modulus) an external video extensometer having a grip distance of 100 mm and a gauge length of 50 mm were used.

Sample 1 was tested 6 times and sample 2 was tested 4 times. Results are shown in Table 1 below.

TABLE 1

Results from testing of tensile modulus.

| Test no. | Sample 1 (release liner alone) | | Sample 2 (release liner + dressing) | |
|---|---|---|---|---|
| | MPa | N/mm | MPa | N/mm |
| 1 | 6000 | 450 | 1606 | 369 |
| 2 | 5400 | 405 | 1843 | 424 |
| 3 | 5082 | 381 | 2037 | 468 |
| 4 | 4109 | 308 | 2073 | 477 |
| 5 | 5378 | 403 | — | — |
| 6 | 5175 | 388 | — | — |
| mean | 5191 | 389 | 1890 | 435 |

In calculation of the MOE in MPa the cross sectional area (the width as well as the thickness) of the sample are highly influential on the results (Modulus equals force divided by cross-sectional area). The values in N/mm are calculated using only the width (Modulus equals force divided by width). The value in N/mm is the most correct value for comparison as sample 2 also includes a layer of adhesive which contributes to the thickness without contributing to the strength. From the table, it appears that the contribution from the backing to the modulus is negligible—approx. 45 N/mm compared to the value of approx. 400 N/mm for the release liner alone. This means that release liner is approx. 10 times more difficult to stretch than the backing and hence the release liner is able to support the dressing during application.

Example

Testing of Peel Strength

The peel strength was also tested at two samples. Sample 1 consisted of the dressing (backing and adhesive) and the release liner with a coating of silicone: Backing PU-film 30 μm, rec. 96 (an adhesive) 120 μm, 75 μm PETP with 1720 silicone. Sample 2 consisted of the same elements but the sample was exposed to radiation at 2×50 kGy. The radiation has the effect of enhancing the adhering of the dressing to the release liner, which corresponds to enhancing the peel strength. The testing was done at an angle of 180° that is the two layers were separated in a direction parallel to the length direction of the sample. The test speed was set to 400 mm/min and the peel strength was calculated between 100-250 mm peeling. The results are given as the force per width; see Table 2 below.

TABLE 2

Results from testing of peel strength.

| Test no. | Sample 1 (no radiation) N/mm | Sample 2 (exposed to radiation) N/mm |
|---|---|---|
| 1 | 0.10 | 1.56 |
| 2 | 0.12 | 1.61 |
| 3 | 0.09 | 1.63 |
| 4 | 0.11 | 1.55 |
| 5 | 0.08 | 1.47 |
| mean | 0.10 | 1.56 |

The peel value obtained on sample 1 corresponds to the most preferred behavior of the dressing. A dressing having a peel value of 0.1 N/mm will be easy to apply without causing wrinkles and will be easy to roll on the skin. The peel value obtained on sample 2 will make the dressing more difficult to apply but it will not be impossible. However, small wrinkles and enclosed air bubbles may occur. A peel value of about 3 N/mm will make it impossible to apply the dressing as described.

The invention claimed is:

1. A method of applying a dressing to skin, the method comprising:
    providing said dressing with a backing layer and an adhesive disposed on a proximal side of the backing layer,
    covering at least a part of the adhesive with a release liner, wherein said backing layer has a proximal side facing the skin during use and wherein said backing layer has a distal side facing away from the skin during use;
    removing a minor portion of the release liner and exposing adhesive on a first part of the dressing;
    adhering the adhesive of the first part of the dressing to the skin;
    folding a second part of the dressing about a folding line so that said distal side of the backing layer in the second part of the dressing faces the skin and said proximal side of said backing layer in the second part of the dressing faces away from the skin;
    pushing a tab of a remaining major portion of the release liner with only one hand from the folding line away from the first part of the dressing in a direction transverse to the folding line and removing the remaining major portion of the release liner from the adhesive on the second part of the dressing as the remaining major portion of the release liner is being pushed; and
    adhering the adhesive on the second part of the dressing to the skin by application of pressure of the only one hand onto the backing layer simultaneously with the pushing step.

2. The method of claim 1, wherein the dressing has a peel strength between the release liner and the adhesive disposed on the proximal side of the backing layer in a range of 0.02 N/mm to 2.0 N/mm at a peel speed setting of 400 mm/min.

3. The method of claim 1, wherein the remaining major portion of the release liner covers between 60% to 95% of the adhesive disposed on the proximal side of the backing layer.

4. The method of claim 1, wherein a modulus of elasticity of the release liner is greater than a modulus of elasticity of the dressing.

5. The method of claim 1, wherein the modulus of elasticity of the release liner is between 200 N/mm and 600 N/mm.

6. The method of claim 1, wherein the release liner has a thickness of 40-150 μm.

7. The method of claim 1, wherein the backing layer has a thickness of 5-50 μm.

8. The method of claim 1, wherein the adhesive has a thickness of 60-300 μm.

9. The method of claim 1, wherein the backing layer has a thickness of 25-35 μm and the adhesive has a thickness of 60-70 μm.

10. The method of claim 1, wherein the dressing has a thickness between 75-85 μm.

11. The method of claim 1, wherein the dressing has an MVTR value of 15-100 mg/cm$^2$/day.

12. A method of applying a dressing to skin, the method comprising:
    providing said dressing with a backing layer,
    disposing an adhesive on a proximal side of the backing layer,
    covering at least a part of the adhesive with a stiffening release liner, wherein said proximal side of said backing layer is facing the skin during use and wherein said backing layer has a distal side facing away from the skin during use;

removing a portion of the stiffening release liner and exposing adhesive of a first part of the dressing;

adhering the adhesive of the first part of the dressing to the skin;

folding a second part of the dressing about a folding line so that said distal side of the backing layer in the second part of the dressing faces the skin and said proximal side of said backing layer in the second part of the dressing faces away from the skin, said second part of the dressing overlying the first part of the dressing in a generally parallel relationship when folded;

pushing a tab of a remaining portion of the stiffening release liner from the folding line away from the first part of the dressing in a direction transverse to the folding line with only one hand;

removing the remaining portion of the stiffening release liner from the adhesive on the second part of the dressing as the remaining portion of the release liner is being pushed away from the first part of the dressing;

adhering the adhesive on the second part of the dressing to the skin as the adhesive on the second part of the dressing is exposed during removal of the remaining portion of the stiffening release layer by rolling of the dressing onto the skin; and applying pressure onto the backing layer simultaneously with the pushing step to adhere the second part of the dressing to the skin.

13. The method of claim 12, wherein a modulus of elasticity of the release liner is greater than a modulus of elasticity of the dressing.

14. The method of claim 12, wherein a modulus of elasticity of the release liner is between 200 N/mm and 600 N/mm.

15. The method of claim 12, wherein the release liner has a thickness of 40-150 μm.

16. The method of claim 12, wherein the backing layer has a thickness of 5-50 μm.

17. The method of claim 12, wherein the adhesive has a thickness of 60-300 μm.

18. The method of claim 12, wherein the backing layer has a thickness of 25-μm and the adhesive has a thickness of 60-70 μm.

19. The method of claim 12, wherein the dressing has a thickness between 75-85 μm.

* * * * *